United States Patent [19]

Matsuda et al.

[11] 4,406,908
[45] Sep. 27, 1983

[54] TETRAZOLYLCOUMARIN DERIVATIVES AND ANTIALLERGIC COMPOSITIONS CONTAINING THE SAME

[75] Inventors: Tetsuo Matsuda, Kyoto; Jun Nakano, Moriyama; Yukio Terashima, Shiga; Yuji Suzuki; Kiyonoshin Itikawa, both of Otsu, all of Japan

[73] Assignee: Kakenyaku Kako Co., Ltd., Tokyo, Japan

[21] Appl. No.: 260,900

[22] Filed: May 6, 1981

[30] Foreign Application Priority Data

May 10, 1980 [JP] Japan .................................. 55-62062

[51] Int. Cl.³ ..................... A61K 31/41; C07D 257/04
[52] U.S. Cl. ..................................... 424/269; 548/253
[58] Field of Search ......................... 548/253; 424/269

[56] References Cited

FOREIGN PATENT DOCUMENTS 2721021 11/1977 Fed. Rep. of Germany ...... 548/251
54-160381 11/1979 Japan .
55-9015 1/1980 Japan .
1434645 5/1976 United Kingdom .

Primary Examiner—Donald G. Daus
Assistant Examiner—D. B. Springer
Attorney, Agent, or Firm—Armstrong, Nikaido, Marmelstein & Kubovcik

[57] ABSTRACT

Tetrazolylcoumarin derivatives of the general formula:

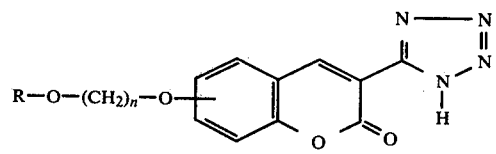

wherein R is hydrogen atom, an alkyl group, an alkenyl group, an alkoxyalkyl group or phenyl group, n is an integer of 2 to 4, and the R—O—(CH$_2$)$_n$—O— group is substituted at any of the 5, 6, 7 and 8 positions of the coumarin ring, and the salts thereof. The compounds are useful as antiallergic agents for preventing and treating allergic diseases.

5 Claims, No Drawings

TETRAZOLYLCOUMARIN DERIVATIVES AND ANTIALLERGIC COMPOSITIONS CONTAINING THE SAME

BACKGROUND OF THE INVENTION

The present invention relates to novel tetrazolylcoumarin derivatives and their salts, and further to a process for the preparation thereof and a pharmaceutical composition containing the tetrazolylcoumarin derivatives or their salts as an active component.

It is known that a certain kind of coumarin derivatives have an antiallergic activity. For instance, Japanese Patent Unexamined Publication No. 64273/1975 discloses that coumarin compounds of the following general formula:

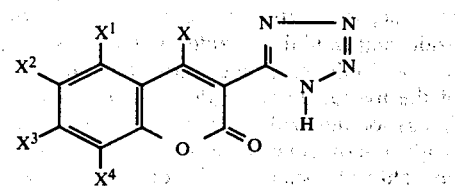

wherein X is an alkyl group or an aryl group, $X^1$, $X^2$, $X^3$ and $X^4$ are the same or different and each is hydrogen, nitro group, an alkyl group, an alkoxyl group, an aryl group, an aralkyl group, a heterocyclic group, a halogen atom, carboxyl group or an acyloxyl group, and any adjacent two groups of $X^1$, $X^2$, $X^3$ and $X^4$ may form a substituted or unsubstituted condensed carbon or heterocyclic ring with the carbon atoms bonding thereto, show an antiallergic action. However, these coumarin derivatives are not always satisfactory antiallergic agents.

It is an object of the present invention to provide novel tetrazolylcoumarin derivatives.

A further object of the invention is to provide tetrazolylcoumarin derivatives useful as antiallergic agents.

A still further object of the invention is to provide a process for preparing tetrazolylcoumarin derivatives.

Another object of the invention is to provide a pharmaceutical composition containing tetrazolylcoumarin derivatives or their salts as active components, which is useful for preventing and treating allergic diseases.

These and other objects of the invention will become apparent from the description hereinafter.

SUMMARY OF THE INVENTION

In accordance with the present invention, there is provided a tetrazolylcoumarin derivative of the following general formula (I):

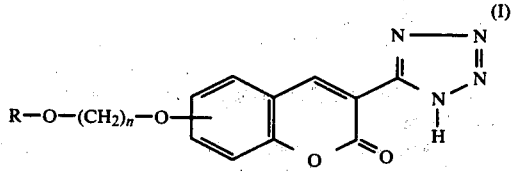

or a salt thereof wherein R is hydrogen atom, an alkyl group, an alkenyl group, an alkoxyalkyl group or phenyl group, n is an integer of 2 to 4, and the R—O—(CH$_2$)$_n$—O— group is substituted at any of the 5, 6, 7 and 8 positions of the coumarin ring.

DETAILED DESCRIPTION

Preferable compounds among the tetrazolylcoumarin derivatives (I) and their salts of the present invention are classified into the following 5 groups:

(1) Tetrazolylcoumarin derivatives defined by the general formula (I) and their salts, in which R is hydrogen atom (hereinafter referred to as "alcohol type derivative")

(2) Tetrazolylcoumarin derivatives defined by the general formula (I) and their salts, in which R is a straight or branched lower alkyl group having 1 to 4 carbon atoms, e.g. methyl, ethyl, propyl, isopropyl, n-butyl, isobutyl, sec-butyl or tertbutyl group (hereinafter referred to as "ether A type derivative")

(3) Tetrazolylcoumarin derivatives defined by the general formula (I) and their salts, in which R is a straight or branched alkenyl group having 2 to 4 carbon atoms, e.g. vinyl, allyl, 1-propenyl, isopropenyl, 1-butenyl, 2-butenyl, 3-butenyl, 1-isobutenyl or 2-isobutenyl group (hereinafter referred to as "ether B type derivative")

(4) Tetrazolylcoumarin derivatives defined by the general formula (I) and their salts, in which R is an alkoxyalkyl group of the following general formula (II):

$$CH_3(CH_2)_l\text{—}O\text{—}(CH_2)_m\text{—} \qquad (II)$$

wherein l is 0 or an integer of 1 to 3 and m is an integer of 2 to 4, e.g. methoxyethyl, methoxypropyl, methoxybutyl, ethoxyethyl, ethoxypropyl, ethoxybutyl, propoxyethyl, propoxypropyl, propoxybutyl, butoxyethyl, butoxypropyl or butoxybutyl group (hereinafter referred to as "ether C type derivative")

(5) Tetrazolylcoumarin derivatives defined by the general formula (I) and their salts, in which R is phenyl group (hereinafter referred to as "ether D type derivative")

The R—O—(CH$_2$)$_n$—O— substituent linking to the coumarin ring may attach to any of the 5, 6, 7 and 8 positions of the coumarin ring, and 8-substituted tetrazolylcoumarin derivatives are particularly preferable.

Typical examples of the alcohol type derivative are, for instance, 8-(3-hydroxypropoxy)-3-(1H-tetrazol-5-yl)coumarin, 8-(4-hydroxybutoxy)-3-(1H-tetrazol-5-yl)-coumarin and their salts.

Typical examples of the ether A type derivative are, for instance, 8-(3-oxabutoxy)-3-(1H-tetrazol-5-yl)comarin, 8-(3-oxapentyloxy)-3-(1H-tetrazol-5-yl)coumarin, 8-(3-oxahexyloxy)-3-(1H-tetrazol-5-yl)-coumarin, 8-(4-methyl-3-oxapentyloxy)-3-(1H-tetrazol-5-yl)coumarin, 8-(3-oxaheptyloxy)-3-(1H-tetrazol-5-yl)coumarin, 8-(5-methyl-3-oxahexyloxy)-3-(1H-tetrazol-5-yl)coumarin, 8-(4-oxahexyloxy)-3-(1H-tetrazol-5-yl)coumarin, 8-(5-oxaheptyloxy)-3-(1H-tetrazol-5-yl)coumarin, 8-(4-oxapentyloxy)-3-(1H-tetrazol-5-yl)coumarin, 8-(4-oxaheptyloxy)-3-(1H-tetrazol-5-yl)coumarin, 8-(5-methyl-4-oxahexyloxy)-3-(1H-tetrazol-5-yl)coumarin, 8-(4-oxaoctyloxy)-3-(1H-tetrazol-5-yl)-coumarin, 8-(6-methyl-4-oxaheptyloxy-3-(1H-tetrazol-5-yl)coumarin, 8-(5-oxahexyloxy)-3-(1H-tetrazol-5-yl)coumarin, 8-(5-oxaoctyloxy)-3-(1H-tetrazol-5-yl)coumarin, 8-(6-methyl-5-oxaheptyloxy)-3-(1H-tetrazol-5-yl)coumarin, 8-(5- oxanonyloxy)-3-(1H-tetrazol-5-yl)coumarin, 8-(7-methyl-5-oxaoctyloxy)-3-(1H-tetrazol-5-yl)coumarin, and their salts.

Typical examples of the ether B type derivative are, for instance, 8-(3-oxa-4-pentenyloxy)-3-(1H-tetrazol-5-yl)coumarin, 8-(3-oxa-5-hexenyloxy)-3-(1H-tetrazol-5-yl)coumarin, 8-(3-oxa-4-hexenyloxy)-3-(1H-tetrazol-5-yl)coumarin, 8-(3-oxa-5-heptenyloxy)-3-(1H-tetrazol-5-yl)coumarin, 8-(4-oxa-6-heptenyloxy)-3-(1H-tetrazol-5-yl)coumarin, 8-(4-oxa-5-octenyloxy)-3-(1H-tetrazol-5-yl)coumarin, 8-(5-oxa-7-octenyloxy)-3-(1H-tetrazol-5-yl)coumarin, 8-(5-oxa-8-nonenyloxy)-3-(1H-tetrazol-5-yl)coumarin, and their salts.

Typical examples of the ether C type derivative are, for instance, 8-(3,6-dioxaheptyloxy)-3-(1H-tetrazol-5-yl)coumarin, 8-(3,7-dioxaoctyloxy)-3-(1H-tetrazol-5-yl)coumarin, 8-(3,6-dioxaoctyloxy)-3-(1H-tetrazol-5-yl)coumarin, 8-(3,7-dioxanonyloxy)-3-(1H-tetrazol-5-yl)coumarin, 8-(3,6-dioxanonyloxy)-3-(1H-tetrazol-5-yl)coumarin, 8-(3,6-dioxadecanyloxy)-3-(1H-tetrazol-5-yl)coumarin, 8-(4,7-dioxaoctyloxy)-3-(1H-tetrazol-5-yl)coumarin, 8-(4,7-dioxanonyloxy)-3-(1H-tetrazol-5-yl)coumarin, 8-(5,8-dioxanonyloxy)-3-(1H-tetrazol-5-yl)coumarin, 8-(5,8-dioxadecanyloxy)-3-(1H-tetrazol-5-yl)coumarin, and their salts.

Typical examples of the ether D type derivative are, for instance, 8-(2-phenoxyethyloxy)-3-(1H-tetrazol-5-yl)coumarin, 8-(3-phenoxypropyloxy)-3-(1H-tetrazol-5-yl)coumarin, 8-(4-phenoxybutyloxy)-3-(1H-tetrazol-5-yl)coumarin, and their salts.

Suitable salts of the tetrazolylcoumarin derivatives shown by the general formula (I) of the present invention are the pharmaceutically acceptable salts, e.g. addition salts with ammonia or an amine such as ethanolamine, methylamine, ethylamine, dimethylamine, diethylamine, triethylamine, dipropylamine or diisopropylamine, and metal salts such as sodium, potassium, aluminum and calcium salts.

The tetrazolylcoumarin derivatives (I) and their salts of the present invention have an excellent inhibitory effect on the isolation of chemical mediators such as histamine and slow reacting substance of anaphylaxis (SRS-A) from mast cells by immune reaction, and they are very useful as medicaments for prevention and treatment of allergic diseases such as allergic asthma, allergic rhinitis, urticaria, idiopathic ulcerative colitis, food allergy and allergic conjunctivitis. In particular, the compounds of the present invention have a marked effect on allergic asthma in oral administration. The effect on the prevention and treatment can be sufficiently exhibited by the dosage of about 0.05 to about 50 mg./day to adult.

The alcohol type derivatives of the present invention are prepared by reacting 3-cyanocoumarin derivatives of the following general formula (IIIa):

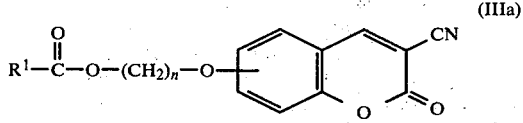

(IIIa)

wherein $R^1$ is an alkyl group having 1 to 3 carbon atoms and n is as defined above, usually 3-cyano-(acetoxyalkoxy)coumarin derivatives, with hydrazoic acid or its salts, and hydrolyzing the resulting product.

The ether A, B, C and D type derivatives of the present invention are prepared by reacting 3-cyanocoumarin derivatives of the following general formula (IIIb):

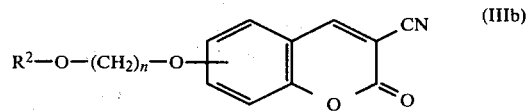

wherein $R^2$ is an alkyl, alkenyl, alkoxyalkyl or phenyl group and n is as defined above, with hydrazoic acid or its salts.

The salts of hydrazoic acid employed in the above reactions include, for instance, alkali metal salts such as lithium azide, sodium azide and potassium azide, alkaline earth metal salts such as magnesium azide, calcium azide, barium azide and strontium azide, other metal salts such as aluminum azide, tin azide, zinc azide and titanium azide, salts with organic bases such as ammonium azide and anilinium azide, and the like. These hydrazoic acid salts may be employed alone, and also, some of the hydrazoic acid salts, e.g. the alkali metal salts such as sodium azide, may be employed in combination with ammonium chloride or a Lewis acid such as aluminum chloride, stannic chloride, zinc chloride or titanium tetrachloride. In that case, the alkali metal salt of hydrazoic acid reacts with ammonium chloride or the Lewis acid to produce another corresponding hydrazoic acid salt such as ammonium azide, aluminum azide, tin azide, zinc azide or titanium azide, and the produced hydrazoic acid salt reacts with the 3-cyanocoumarin derivative (IIIa) or (IIIb). The combination use of the hydrazoic acid alkali metal salt with ammonium chloride or the Lewis acid produces a particularly good result.

The amounts of hydrazoic acid or its salts and the Lewis acids or ammonium chloride to be used in combination with the hydrazoic acid alkali metal salts are usually selected from 1 to 10 moles per mole of the 3-cyanocoumarin derivative (IIIa) or (IIIb), respectively.

The reaction is usually carried out in an organic solvent such as hydrocarbons, e.g. benzene, toluene and petroleum ether, ethers, e.g. tetrahydrofuran, dioxane and ethyl ether, or aprotic polar solvents, e.g. dimethylformamide and dimethyl sulfoxide.

The reaction conditions such as temperature and time are not particularly limited, but the reaction is usually carried out at a temperature of from room temperature to 130° C. for 30 minutes to 24 hours.

When the hydrazoic acid salt is employed in the reaction, the product is in the form of a salt corresponding to the hydrazoic acid salt used in the reaction, on the basis of the acidic property of the tetrazolyl group. The salt may be isolated as it is, or may be treated with a mineral acid such as hydrochloric acid or sulfuric acid to give the compound of the general formula (I) having a free tetrazolyl group.

The products may be isolated and purified in a usual manner, such as fractionation based on dissociation of hydrogen of tetrazolyl group, chromatography or recrystallization.

Some salts of the tetrazolylcoumarin derivatives (I) of the invention are directly obtained by the above reaction. The salts of the tetrazolylcoumarin derivatives (I) may also be obtained by once isolating the tetrazolylcoumarin derivatives (I) and reacting them with a corresponding base.

Most of the 3-cyanocoumarin derivatives (IIIa) and (IIIb) employed as starting materials for preparing the tetrazolylcoumarin derivatives (I) and their salts of the invention are novel compounds.

The 3-cyanocoumarin derivatives (IIIa) and (IIIb) can be prepared by reacting o-hydroxybenzaldehyde derivatives with cyanomalonic esters, e.g. cyanomalonic esters with lower alcohols such as methyl alcohol and ethyl alcohol, or malononitrile. In case of preparing the 3-cyanocoumarin derivatives (IIIa), compounds of the following general formula (IVa):

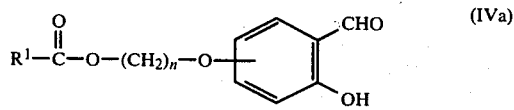

wherein $R^1$ and n are as defined above, are employed as the above o-hydroxybenzaldehyde derivatives, and in case of preparing the 3-cyanocoumarin derivatives (IIIb), compounds of the following general formula (IVb):

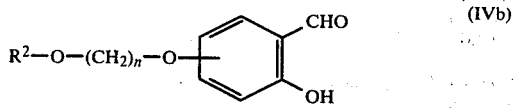

wherein $R^2$ and n are as defined above, are employed as the above o-hydroxybenzaldehyde derivatives.

It is also possible to prepare the 3-cyanocoumarin derivatives (IIIa) and (IIIb) by employing, as a starting material, 3-cyano-hydroxycoumarin of formula (V):

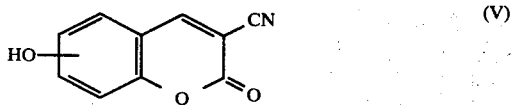

wherein OH group is substituted at the 5, 6, 7 or 8 position of the coumarin ring. The 3-cyano-hydroxycoumarin (V) is reacted in the presence of alkali metal hydrides such as sodium hydride and potassium hydride with halogen compounds of the following general formula (VIa):

wherein $R^1$ and n are as defined above and X is a halogen atom, to produce the 3-cyanocoumarin derivatives (IIIa), or with halogen compounds of the following general formula (VIb):

wherein $R^2$, n and X are as defined above, to produce the 3-cyanocoumarin derivatives (IIIb). Also, the 3-cyanocoumarin derivatives (IIIb) can be prepared by subjecting the 3-cyano-hydroxycoumarin (V) to dehydration condensation with alcohols of the following general formula (VII):

wherein $R^2$ and n are as defined above, in the presence of triphenylphosphine and diethyl azodicarboxylate.

The tetrazolylcoumarin derivatives (I) and their salts of the present invention have excellent activities, particularly an excellent antiallergic activity. Accordingly, the tetrazolylcoumarin derivatives (I) and their pharmaceutically acceptable salts are very useful as antiallergic agents. They can be formulated in a usual manner into compositions in the form of tablet, capsule, powder and granule with conventional pharmaceutical carriers. They are also usable as an aerosol in the form of solution or suspension. The salts of the tetrazolylcoumarin derivatives (I) are soluble in water and, therefore, can also be employed in liquid form such as for injections, syrup, nasal drops or ophthalmic solution. Any conventional carriers employed in preparing preparations can be employed in the present invention. Examples of the carrier are binders, solid diluents, liquid diluents, fillers, and the like, e.g. starch, lactose, microcrystalline cellulose, sugar, magnesium stearate, silicon dioxide, talc and physiological salt solution.

The present invention is more particularly described and explained by means of the following Examples, in which all % and parts are by weight unless otherwise noted. In order to illustrate the preparation of the 3-cyanocoumarin derivatives (IIIa) and (IIIb) employed as starting materials for preparing the tetrazolylcoumarin derivatives (I) and their salts of the invention, the following Reference Examples are also presented.

REFERENCE EXAMPLE 1

[3-Cyano-8-(3-acetoxypropoxy)coumarin]

In 150 ml. of dry dimethylformamide was dissolved 9.35 g. of 3-cyano-8-hydroxycoumarin. To the resulting solution was added 2.5 g. of about 60% sodium hydride with agitation and ice-cooling, and after raising to room temperature, the solution was agitated for 20 minutes. After adding dropwise 9.05 g. of 3-acetoxypropyl bromide at a temperature of 80° to 90° C. with agitation, the reaction was carried out for 5 hours with agitation. After the completion of the reaction, the reaction mixture was poured into 200 ml. of water added with ice, and extracted with three 200 ml. portions of methylene chloride. The obtained extract was dried with magnesium sulfate, and the solvent was then distilled away under reduced pressure. The residue was purified by a silica-gel column chromatography (silica-gel: 350 g., eluent: methylene chloride) to give 3-cyano-8-(3-acetoxypropoxy)coumarin (yield: 25%). The product was further recrystallized from ethyl acetate to give light yellow needles having a melting point of 132° to 135° C.

Analysis for $C_{15}H_{13}NO_5$: Calcd. (%): C 62.71, H 4.56, N 4.88: Found (%): C 62.48, H 4.64, N 4.63.

Infrared absorption spectrum ($\nu_{max}^{KBr}$ cm.$^{-1}$): 2210 (CN), 1730 and 1725 (C=O), 1600 and 1570 (C=C)

Mass spectrum (M/e):
287 (M+), 244, 227, 198, 187 and 159

REFERENCE EXAMPLES 2 TO 12

The procedures of Reference Example 1 were repeated except that halogen compounds shown in Table 1 were employed instead of 3-acetoxypropyl bromide to give the following products.

The results are also shown below, in which the yield shows a yield of a product before recrystallization and the solvent enclosed in parentheses after crystal form shows solvent used in recrystallization.

TABLE 1

| Ref. Ex. No. | Halogen compound |
|---|---|
| 2 | 3-oxabutyl bromide |
| 3 | 3-oxapentyl bromide |
| 4 | 3-oxahexyl bromide |
| 5 | 4-methyl-3-oxapentyl bromide |
| 6 | 3-oxaheptyl bromide |
| 7 | 5-methyl-3-oxahexyl bromide |
| 8 | 4-oxahexyl bromide |
| 9 | 5-oxaheptyl bromide |
| 10 | 3-oxa-5-hexenyl bromide |
| 11 | 3,6-dioxaoctyl bromide |
| 12 | 2-phenoxyethyl bromide |

(Ref. Ex. 2) 3-Cyano-8-(3-oxabutoxy)coumarin
Yield: 29%
Yellow needles (ethyl acetate)
Melting point: 138° to 141° C.
Analysis for $C_{13}H_{11}NO_4$:
    Calcd. (%)      C 63.67,      H 4.52,      N 5.71
    Found (%)      C 63.57,      H 4.58,      N 5.66
Infrared absorption spectrum $(\nu_{max}^{KBr}$ cm.$^{-1})$:
2210 (CN), 1730 (C=O), 1600 and 1570 (C=C)
Mass spectrum (M/e):
245 (M$^+$), 214, 201, 187 and 159

(Ref. Ex. 3) 3-Cyano-8-(3-oxapentyloxy)coumarin
Yield: 31%
Yellow needles (ethyl acetate)
Melting point: 105° to 109° C.
Analysis for $C_{14}H_{13}NO_4$:
    Calcd. (%)      C 64.86,      H 5.05,      N 5.40
    Found (%)      C 64.71,      H 5.09,      N 5.35
Infrared absorption spectrum $(\nu_{max}^{KBr}$ cm.$^{-1})$:
2250 (CN), 1740 (C=O), 1610 and 1570 (C=C)
Mass spectrum (M/e):
259 (M$^+$), 215, 200, 187 and 159

(Ref. Ex. 4) 3-Cyano-8-(3-oxahexyloxy)coumarin
Yield: 28%
Light yellow needles (ethyl acetate)
Melting point: 96° to 99° C.
Analysis for $C_{15}H_{15}NO_4$:
    Calcd. (%)      C 65.92,      H 5.53,      N 5.13
    Found (%)      C 65.78,      H 6.67,      N 5.02
Infrared absorption spectrum $(\nu_{max}^{KBr}$ cm.$^{-1})$:
2240 (CN), 1740 (C=O), 1610 and 1570 (C=C)
Mass spectrum (M/e):
273 (M$^+$), 244, 214, 200, 187 and 159

(Ref. Ex. 5) 3-Cyano-8-(4-methyl-3-oxapentyloxy)coumarin
Yield: 28%
Light yellow needles (ethyl acetate)
Melting point: 113° to 116° C.
Analysis for $C_{15}H_{15}NO_4$:
    Calcd. (%)      C 65.92,      H 5.53,      N 5.13
    Found (%)      C 65.76,      H 5.66,      N 5.01
Infrared absorption spectrum $(\nu_{max}^{KBr}$ cm.$^{-1})$:
2240 (CN), 1720 (C=O), 1605 and 1570 (C=C)
Mass spectrum (M/e):
273 (M$^+$), 257, 231, 214, 200, 187 and 159

(Ref. Ex. 6) 3-Cyano-8-(3-oxaheptyloxy)coumarin
Yield: 29%
Yellow needles (benzene)
Melting point: 66° to 67° C.
Analysis for $C_{16}H_{17}NO_4$:
    Calcd. (%)      C 66.65,      H 6.11,      N 4.63
    Found (%)      C 66.88,      H 5.96,      N 4.88
Infrared absorption spectrum $(\nu_{max}^{KBr}$ cm.$^{-1})$:
2240 (CN), 1730 (C=O), 1605 and 1570 (C=C)
Mass spectrum (M/e):
287 (M$^+$), 244, 231, 214, 200, 187 and 159

(Ref. Ex. 7) 3-Cyano-8-(5-methyl-3-oxahexyloxy)coumarin
Yield: 26%
Light yellow needles (benzene)
Melting point: 60° to 62° C.
Analysis for $C_{16}H_{17}NO_4$:
    Calcd. (%)      C 66.88,      H 5.96,      N 4.88
    Found (%)      C 66.74,      H 6.04,      N 4.69

TABLE 1-continued

| Ref. Ex. No. | Halogen compound |
|---|---|

Infrared absorption spectrum $(\nu_{max}^{KBr}$ cm.$^{-1})$:
2220 (CN), 1720 (C=O), 1600 and 1570 (C=C)
Mass spectrum (M/e):
287 (M$^+$), 244, 231, 214, 200, 187 and 159

(Ref. Ex. 8) 3-Cyano-8-(4-oxahexyloxy)coumarin
Yield: 30%
Light yellow needles (ethyl acetate)
Melting point: 107° to 108° C.
Analysis for $C_{15}H_{15}NO_4$:
    Calcd. (%)      C 65.92,      H 5.53,      N 5.13
    Found (%)      C 65.78,      H 5.71,      N 5.04
Infrared absorption spectrum $(\nu_{max}^{KBr}$ cm.$^{-1})$:
2220 (CN), 1740 (C=O), 1610 and 1570 (C=C)
Mass spectrum (M/e):
273 (M$^+$), 229, 211, 199, 187 and 159

(Ref. Ex. 9) 3-Cyano-8-(5-oxaheptyloxy)coumarin
Yield: 29%
Light yellow needles (benzene)
Melting point: 93° to 95° C.
Analysis for $C_{16}H_{17}NO_4$:
    Calcd. (%)      C 66.88,      H 5.96,      N 4.88
    Found (%)      C 66.56,      H 6.07,      N 4.59
Infrared absorption spectrum $(\nu_{max}^{KBr}$ cm.$^{-1})$:
2240 (CN), 1735 (C=O), 1610 and 1570 (C=C)
Mass spectrum (M/e):
288 (M$^+$), 243, 228, 213, 200, 187 and 159

(Ref. Ex. 10) 3-Cyano-8-(3-oxa-5-hexenyloxy)coumarin
Yield: 28%
Yellow needles (ethyl acetate)
Melting point: 78° to 80° C.
Analysis for $C_{15}H_{13}NO_4$:
    Calcd. (%)      C 66.41,      H 4.83,      N 5.16
    Found (%)      C 66.23,      H 4.95,      N 5.01
Infrared absorption spectrum $(\nu_{max}^{KBr}$ cm.$^{-1})$:
2225 (CN), 1730 (C=O), 1610 and 1565 (C=C)
Mass spectrum (M/e):
271 (M$^+$), 240, 213, 187, 170 and 159

(Ref. Ex. 11) 3-Cyano-8-(3,6-dioxaoctyloxy)coumarin
Yield: 27%
Light yellow needles (benzene)
Melting point: 130° C.
Analysis for $C_{16}H_{17}NO_5$:
    Calcd. (%)      C 63.36,      H 5.65,      N 4.62
    Found (%)      C 63.03,      H 5.81,      N 4.33
Infrared absorption spectrum $(\nu_{max}^{KBr}$ cm.$^{-1})$:
2220 (CN), 1740 (C=O), 1605 and 1570 (C=C)
Mass spectrum (M/e):
303 (M$^+$), 259, 231, 213, 201, 187 and 159

(Ref. Ex. 12) 3-Cyano-8-(2-phenoxyethyloxy)coumarin
Yield: 30%
Light yellow needles (ethyl acetate)
Melting point: 178° to 181° C.
Analysis for $C_{18}H_{13}NO_4$:
    Calcd. (%)      C 70.35,      H 4.26,      N 4.56
    Found (%)      C 70.09,      H 4.41,      N 4.35
Infrared absorption spectrum $(\nu_{max}^{KBr}$ cm.$^{-1})$:
2240 (CN), 1720 (C=O), 1600 and 1570 (C=C)
Mass spectrum (M/e):
307 (M$^+$), 214, 188, 170 and 121

REFERENCE EXAMPLE 13

[3-Cyano-8-(3-oxabutoxy)coumarin]

In 200 ml. of anhydrous tetrahydrofuran were dissolved 18.7 g. of 3-cyano-8-hydroxycoumarin, 11.4 g. of 3-oxabutanol and 39.3 g. of triphenylphosphine. To this solution was then added dropwise 22.6 g. of diethyl azodicarboxylate at room temperature with agitation. The rate of the dropwise addition was controlled so as to maintain the reaction temperature at less than 50° C. due to exothermic reaction. After the addition, the reaction mixture was allowed to stand for 2 hours to further continue the reaction.

The solvent was distilled away under reduced pressure, and 200 ml. of ether was added to the residue and the resulting precipitate was removed by filtration. The filtrate was evaporated, and 200 ml. of a mixed solvent of ether and pentane (1:1 by volume) was added to the obtained residue and the resulting precipitate (brown precipitate I) was recovered by filtration. Further, the obtained filtrate was evaporated, and the precipitate (brown precipitate II) formed by adding 200 ml. of the ether-pentane mixed solvent to the evaporated residue was recovered by filtration. The precipitates I and II were put together and washed with two 200 ml. portions of a mixed solvent of isopropanol and pentane (1:2 by volume) to give 17.4 g. of 3-cyano-8-(3-oxabutoxy)-coumarin. The yield was 91%.

REFERENCE EXAMPLES 14 TO 23

The same 3-cyanocoumarin derivatives as those prepared in Reference Examples 3 to 12 were prepared in the same manner as in Reference Example 13 except that alcohols shown in Table 2 were employed instead of 3-oxabutanol.

The alcohols, products and yields are shown in Table 2 together with the result in Reference Example 13.

TABLE 2

| Ref Ex. No. | Alcohol | 3-Cyanocoumarin derivative | Yield (%) |
|---|---|---|---|
| 13 | 3-oxabutanol | 3-cyano-8-(3-oxabutoxy)coumarin | 91 |
| 14 | 3-oxapentyl alcohol | 3-cyano-8-(3-oxapentyloxy)coumarin | 90 |
| 15 | 3-oxahexyl alcohol | 3-cyano-8-(3-oxahexyloxy)coumarin | 94 |
| 16 | 4-methyl-3-oxapentyl alcohol | 3-cyano-8-(4-methyl-3-oxapentyloxy)coumarin | 89 |
| 17 | 3-oxaheptyl alcohol | 3-cyano-8-(3-oxaheptyloxy)coumarin | 89 |
| 18 | 5-methyl-3-oxahexyl alcohol | 3-cyano-8-(5-methyl-3-oxahexyloxy)coumarin | 88 |
| 19 | 4-oxahexyl alcohol | 3-cyano-8-(4-oxahexyloxy)coumarin | 91 |
| 20 | 5-oxaheptyl alcohol | 3-cyano-8-(5-oxaheptyloxy)coumarin | 90 |
| 21 | 3-oxa-5-hexenyl alcohol | 3-cyano-8-(3-oxa-5-hexenyloxy)coumarin | 93 |
| 22 | 3,6-dioxaoctyl alcohol | 3-cyano-8-(3,6-dioxaoctyloxy)coumarin | 89 |
| 23 | 2-phenoxyethanol | 3-cyano-8-(2-phenoxyethyloxy)coumarin | 90 |

EXAMPLE 1

[8-(3-Hydroxypropoxy)-3-(1H-tetrazol-5-yl)coumarin]

To 25 ml. of anhydrous tetrahydrofuran was added 4 g. of aluminum chloride with ice cooling, and further 5.9 g. of sodium azide and 2.87 g. of 3-cyano-8-(3-acetoxypropoxy)coumarin obtained in Reference Example 1 were added in that order. The mixture was refluxed for 5 hours with agitation. After the completion of the reaction, the reaction mixture was poured into 200 ml. of 10% hydrochloric acid added with ice and was thoroughly agitated. The resulting precipitate was filtered and was then added to 70 ml. of a saturated aqueous solution of sodium hydrogencarbonate, and the hydrolysis was carried out at 70° C. for 1 hour with agitation. After removing impurities by filtration, a concentrated hydrochloric acid was gradually added dropwise to the filtrate to adjust to pH 3 to 4, and the resulting precipitate was filtered. The obtained light yellow precipitate was recrystallized from a dimethylformamide-water mixed solvent (3:1 by volume) (hereinafter referred to as "DMF-H$_2$O") to give 2.02 g. of 8-(3-hydroxypropoxy)-3-(1H-tetrazol-5-yl)coumarin in the form of light yellow needles (yield: 70%). The melting point was 266° C. (decomposition).

Analysis for $C_{13}H_{12}N_4O_4$: Calcd. (%): C 54.17, H 4.17, N 19.46: Found (%): C 53.93, H 4.31, N 19.18.

Infrared absorption spectrum ($\nu_{max}^{KBr}$ cm.$^{-1}$): 3450, 3350 (OH, NH), 1720 (C=O), 1625 and 1610 (C=C)

Mass spectrum (M/e): 288 (M$^+$), 264, 230, 206, 187, 174 and 144

EXAMPLE 2

[8-(3-Oxabutoxy)-3-(1H-tetrazol-5-yl)coumarin]

To 30 ml. of anhydrous tetrahydrofuran was added 4.82 g. of aluminum chloride with ice cooling, and further 7.02 g. of sodium azide and 2.94 g. of 3-cyano-8-(3-oxabutoxy)coumarin obtained in Reference Example 2 were added in that order. The mixture was refluxed for 5 hours with agitation. After the completion of the reaction, the reaction mixture was poured into 200 ml. of 10% hydrochloric acid added with ice and was thoroughly agitated. The resulting precipitate was filtered and was then added to 70 ml. of a saturated aqueous solution of sodium hydrogencarbonate. The precipitate was dissolved with heating and agitation, and an insoluble material was removed by filtration. The filtrate was adjusted to pH 3 to 4 by gradually adding dropwise a concentrated hydrochloric acid, and the resulting precipitate was filtered. The obtained light yellow precipitate was dissolved in a DMF-H$_2$O mixed solvent (3:1 by volume), and after treating with active carbon, was recrystallized to give 2.6 g. of 8-(3-oxabutoxy)-3-(1H-tetrazol-5-yl)coumarin in the form of light yellow needles (yield: 74%). The melting point was 215° C.

Analysis for $C_{13}H_{12}N_4O_4$: Calcd. (%): C 54.16, H 4.20, N 19.44: Found (%): C 54.02, H 4.28, N 19.33.

Infrared absorption spectrum ($\nu_{max}^{KBr}$ cm.$^{-1}$): 3150 (NH), 1720 (C=O), 1620 and 1610 (C=C)

Mass spectrum (M/e): 288 (M$^+$), 274, 257, 243 and 230

EXAMPLES 3 TO 12

The procedures of Example 2 were repeated except that there were employed as starting materials the 3-cyanocoumarin derivatives obtained in Reference Examples 3 to 12, i.e. 3-cyano-8-(3-oxapentyloxy)coumarin (Ex. 3), 3-cyano-8-(3-oxahexyloxy)coumarin (Ex. 4), 3-cyano-8-(4-methyl-3-oxapentyloxy)coumarin (Ex. 5), 3-cyano-8-(3-oxaheptyloxy)coumarin (Ex. 6), 3-cyano-8-(5-methyl-3-oxahexyloxy)coumarin (Ex. 7), 3-cyano-8-(4-oxahexyloxy)coumarin (Ex. 8), 3-cyano-8-(5-oxaheptyloxy)coumarin (Ex. 9), 3-cyano-8-(3-oxa-5-hexenyloxy)coumarin (Ex. 10), 3-cyano-8-(3,6-dioxaoctyloxy)coumarin (Ex. 11), and 3-cyano-8-(2-phenoxyethyloxy)coumarin (Ex. 12).

The results are shown below, in which the yield shows a yield of a product obtained after recrystallization.

(Ex. 3) 8-(3-Oxapentyloxy)-3-(1H-tetrazol-5-yl)coumarin
Yield: 78%
Colorless needles [DMF-$H_2O$ (4:1 by volume)]
Melting point: 203° to 204° C.
Analysis for $C_{14}H_{14}N_4O_4$: Calcd. (%): C 55.62, H 4.67, N 18.54: Found (%): C 55.38, H 4.77, N 18.25.
Infrared absorption spectrum ($\nu_{max}^{KBr}$ cm.$^{-1}$): 3150 (NH), 1700 (C=O), 1620 and 1610 (C=C)
Mass spectrum (M/e): 302 (M+), 274, 258, 242 and 230

(Ex. 4) 8-(3-Oxahexyloxy)-3-(1H-tetrazol-5-yl)coumarin
Yield: 78%
Colorless needles [DMF-$H_2O$ (4:1 by volume)]
Melting point: 185° C.
Analysis for $C_{15}H_{16}N_4O_4$: Calcd. (%): C 56.96, H 5.10, N 17.71: Found (%): C 56.74, H 5.23, N 17.58.
Infrared absorption spectrum ($\nu_{max}^{KBr}$ cm.$^{-1}$): 3240 (NH), 1720 (C=O), 1615 and 1610 (C=C)
Mass spectrum (M/e): 302 (M+), 274, 258, 242 and 230

(Ex. 5) 8-(4-Methoxy-3-oxapentyloxy)-3-(1H-tetrazol-5-yl)coumarin
Yield: 74%
Colorless needles [DMF-$H_2O$ (4:1 by volume)]
Melting point: 188° to 189° C.
Analysis for $C_{15}H_{16}N_4O_4$:
Calcd. (%): C 56.96, H 5.10, N 17.71: Found (%): C 56.72, H 5.18, N 17.53.
Infrared absorption spectrum ($\nu_{max}^{KBr}$ cm.$^{-1}$): 3250 (NH), 1720 (C=O), 1630 and 1610 (C=C)
Mass spectrum (M/e): 316 (M+), 301, 285, 274, 258, 243 and 230

(Ex. 6) 8-(3-Oxaheptyloxy)-3(1H-tetrazol-5-yl)coumarin
Yield: 74%
Colorless needles (ethyl acetate)
Melting point: 163° C.
Analysis for $C_{16}H_{18}N_4O_4$: Calcd. (%): C 58.16, H 5.49, N 16.96 Found (%): C 58.02, H 5.63, N 16.68
Infrared absorption spectrum ($\nu_{max}^{KBr}$ cm.$^{-1}$): 3150 (NH), 1730 (C=O), 1630 and 1610 (C=C)
Mass spectrum (M/e): 330 (M+), 316, 287, 274, 243 and 230

(Ex. 7) 8-(5-Methyl-3-oxahexyloxy)-3-(1H-tetrazol-5-yl)coumarin
Yield: 77%
Colorless needles (ethyl acetate)
Melting point: 186° C.
Analysis for $C_{16}H_{18}N_4O_4$: Calcd. (%): C 58.17, H 5.49, N 16.96; Found (%): C 57.93, H 5.74, N 16.79.
Infrared absorption spectrum ($\nu_{max}^{KBr}$ cm.$^{-1}$): 3175 (NH), 1730 (C=O), 1625 and 1611 (C=C)
Mass spectrum (M/e): 330 (M+), 286, 274, 243 and 230

(Ex. 8) 8-(4-Oxahexyloxy)-3-(1H-tetrazol-5-yl)coumarin
Yield: 78%
Colorless needles [DMF-$H_2O$ (4:1 by volume)]
Melting point 180° to 181° C.
Analysis for $C_{15}H_{16}N_4O_4$: Calcd. (%): C 56.96, H 5.10, N 17.71: Found (%): C 56.71, H 5.23, N 17.45.
Infrared absorption spectrum ($\nu_{max}^{KBr}$ cm.$^{-1}$): 3170 (NH), 1730 (C=O), 1625 and 1610 (C=C)
Mass spectrum (M/e): 316 (M+), 288, 272, 257 and 243

(Ex. 9) 8-(5-Oxaheptyloxy)-3-(1H-tetrazol-5-yl)coumarin
Yield: 78%
Colorless needles (ethyl acetate)
Melting point: 180° to 181° C.
Analysis for $C_{16}H_{18}N_4O_4$: Calcd. (%): C 58.17, H 5.49, N 16.96: Found (%): C 59.96, H 5.63, N 16.71.
Infrared absorption spectrum ($\nu_{max}^{KBr}$ cm.$^{-1}$): 3150 (NH), 1730 (C=O), 1620 and 1610 (C=C)
Mass spectrum (M/e): 330 (M+), 302, 286, 231 and 187

(Ex. 10) 8-(3-Oxa-5-hexenyloxy)-3-(1H-tetrazol-5-yl)-coumarin
Yield: 79%
Light yellow needles [DMF-$H_2O$ (3:1 by volume)]
Melting point: 175° C.
Analysis for $C_{15}H_{14}N_4O_4$: Calcd. (%): C 57.32, H 4.49, N 17.83; Found (%): C 57.09, H 4.61, N 17.66.
Infrared absorption spectrum ($\nu_{max}^{KBr}$ cm.$^{-1}$): 3210 (NH), 1715 (C=O), 1630 and 1610 (C=C)
Mass spectrum (M/e): 314 (M+), 283, 270, 258, 230 and 202

(Ex. 11) 8-(3,6-Dioxaoctyloxy)-3-(1-H-tetrazol-5-yl)-coumarin
Yield: 75%
Colorless needles (ethyl acetate)
Melting point: 145° C.
Analysis for $C_{16}H_{18}N_4O_5$: Calcd. (%): C 55.43, H 5.24, N 16.18: Found (%): C 55.21, H 5.36, N 16.03.
Infrared absorption spectrum ($\nu_{max}^{KBr}$ cm.$^{-1}$): 3200 (NH), 1730 (C=O), 1630 and 1610 (C=C)
Mass spectrum (M/e): 346 (M+), 303, 288, 274, 258, 256 and 214

(Ex. 12) 8-(2-Phenoxyethyloxy)-3-(1H-tetrazol-5-yl)-coumarin
Yield: 78%
Colorless needles [DMF-$H_2O$ (3:1 by volume)]
Melting point: 227° to 229° C.
Analysis for $C_{18}H_{14}N_4O_4$: Calcd. (%): C 61.71, H 4.03, N 16.00: Found (%): C 61.57, H 4.14, N 15.77.
Infrared absorption spectrum ($\nu_{max}^{KBr}$ cm.$^{-1}$): 3150 (NH), 1695 (C=O), 1620, 1605 and 1580 (C=C)
Mass spectrum (M/e): 350 (M+), 307, 214 and 121

EXAMPLE 13

[Sodium salt of 8-(3-oxahexyloxy)-3-(1H-tetrazol-5-yl)-coumarin]

To 5 ml. of a saturated aqueous solution of sodium hydrogencarbonate was added 1 g. of 8-(3-oxahexyloxy)-3-(1H-tetrazol-5-yl)coumarin obtained in Example 4, and after adding 20 ml. of water, was dissolved with heating. To the solution was then added 10 ml. of ethanol, and the resulting precipitate was immediately dissolved again by heating. After filtering the solution, the filtrate was allowed to stand at room temperature. The resulting precipitate was filtered and dried to give 0.9 g. of sodium salt of 8-(3-oxahexyloxy)-3-(1H-tetrazol-5-yl)coumarin in the form of colorless powder (yield: 83%). The melting point was not less than 330° C.

EXAMPLE 14

[Sodium salt of 8-(5-methyl-3-oxahexyloxy)-3-(1H-tetrazol-5-yl)coumarin]

The procedure of Example 13 was repeated except that 1 g. of 8-(5-methyl-3-oxahexyloxy)-3-(1H-tetrazol-5-yl)coumarin obtained in Example 7 was employed instead of 8-(3-oxabutoxy)-3-(1H-tetrazol-5-yl)coumarin, to give 0.9 g. of colorless powder of sodium salt of 8-(5-methyl-3-oxahexyloxy)-3-(1H-tetrazol-5-yl)coumarin (yield: 84%). The melting point was not less than 330° C.

EXAMPLE 15

[Diethylamine salt of 8-(3-oxabutoxy)-3-(1H-tetrazol-5-yl)coumarin]

In 40 ml. of an ethanol-diethylamine mixed solvent (3:1 by volume) was heat-dissolved 1 g. of 8-(3-oxabutoxy)-3-(1H-tetrazol-5-yl)coumarin obtained in Example 2. The solvent was then distilled away, and the residue was washed with ethyl ether, filtered and dried to give 1.1 g. of colorless powder of diethylamine salt of 8-(3-oxabutoxy)-3-(1H-tetrazol-5-yl)coumarin (yield: 88%). The melting point was 171° C.

EXAMPLE 16

[Diethylamine salt of

The procedure of Example 15 was repeated except that 1 g. of 8-(4-oxahexyloxy)-3-(1H-tetrazol-5-yl)coumarin obtained in Example 8 was employed instead of 8-(3-oxabutoxy)-3-(1H-tetrazol-5-yl)coumarin, to give 1.1 g. of colorless powder of diethylamine salt of 8-(4-oxahexyloxy)-3-(1H-tetrazol-5-yl)coumarin (yield: 89%). The melting point was 147° to 148° C.

EXAMPLE 17

A mixture of 5 parts of 8-(4-oxahexyloxy)-3-(1H-tetrazol-5-yl)coumarin, 30 parts of lactose, 45 parts of corn starch, 15 parts of microcrystalline cellulose (commercially available under the registered trade mark "Avicel" made by Asahi Chemical Industry Co., Ltd.), 3 parts of methyl cellulose and 2 parts of magnesium stearate was thoroughly blended and then screened through a 50 mesh screen. The resulting powder was tabletted by an automatic tabletting machine to give tablets containing 5 mg. of the essential active ingredient per one tablet of 100 mg.

EXAMPLE 18

A mixture of 5 parts of 8-(5-methyl-3-oxahexyloxy)-3-(1H-tetrazol-5-yl)coumarin, 55 parts of lactose, 30 parts of corn starch, 8 parts of Avicel and 2 parts of magnesium stearate was thoroughly blended. The mixture was then filled in capsules made of gelatin to give capsules containing 5 mg. of the essential active ingredient per one capsule.

EXAMPLE 19

In 1,000 ml. of a physiological salt solution was dissolved 2 g. of 8-(3-oxabutoxy)-3-(1H-tetrazol-5-yl)coumarin sodium salt. The solution was adjusted to pH 7.4 to give an injection.

EXAMPLE 20

A nasal drops was prepared by dissolving in 1,000 ml. of distilled water 2 g. of 8-(3-oxabutoxy)-3-(1H-tetrazol-5-yl)coumarin sodium salt, 0.1 g. of methyl p-hydroxybenzoate, 0.1 g. of butyl p-hydroxybenzoate and 7.5 g. of sodium chloride.

EXAMPLE 21

An ophthalmic solution was prepared by dissolving in distilled water 0.5 g. of 8-(4-oxahexyloxy)-3-(1H-tetrazol-5-yl)coumarin sodium salt, 0.1 g. of sodium dihydrogenphosphate, 1.25 g. of disodium hydrogenphosphate and 0.3 g. of sodium chloride, and adjusting the total volume to 100 ml.

EXAMPLE 22

According to the following formulation, an aerosol was prepared as follows:

| Components | Amount (%) |
| --- | --- |
| 8-(3-Oxaheptyloxy)-3-(1H—tetrazol-5-yl)coumarin | 0.5 |
| Ethanol | 29.5 |
| Dichlorodifluoromethane (propellant) | 42.0 |
| 1,2-Dichlorotetrafluoroethane (propellant) | 28.0 |

In ethanol was dissolved 8-(3-oxaheptyloxy)-3-(1H-tetrazol-5-yl)coumarin, and the solution was placed in a container for aerosol. The propellant was then supplied to the container through a valve nozzle under pressure until the inner pressure became 2.5 to 3.5 kg./cm.$^2$G at 20° C.

EXAMPLE 23

With respect to the 3-(1H-tetrazol-5-yl)-coumarin derivatives obtained in Examples 1 to 12, there was tested antiallergic activity concerning passive cutaneous anaphylaxis (PCA) mediated by homocytotropic antibodies (HTA) in rats.

(1) METHODS (i) Preparation of antisera 2,4-Dinitrophenyl-coupled ascaris extract (DNP-As) used as antigen, was prepared according to the methods of Strejan et al [cf. J. Immunol., Vol. 98, 893(1967)] and Eisen [cf. J. Amer. Chem. Soc., Vol. 75, 4593(1953)]. Antisera containing HTA were prepared in rats according to the method of Tada and Okumura [cf. J. Immunol., Vol. 106, 1002(1971)] as follows:

Wister rats weighing 180 to 200 g. were splenectomized and several days later immunized by injecting into all four footpads a total of 1 mg. of DNP-As mixed with $10^{10}$ *Bordetella pertussis*. After 5 days, 0.5 mg. of DNP-As alone was injected subcutaneously into the back of rats. Eight days after the first immunization, blood was collected by aortic puncture under ether anaesthesea and antisera obtained by these procedures were pooled and stored at −80° C.

The titer of the pooled autiserum was determined in rats by the 72 hr. PCA which method was described in the following item (ii), i.e. the highest dilution of antiserum producing a diameter of approximately 5 mm. was usually 1:500.

(ii) Assessment of PCA in rats

Normal wister rats weighing 140 to 160 g. were sensitized passively by injection intradermal on the shaved back skin 0.05 ml. of the diluted antisera (1:30). After 72 hours, the animals were injected intravenously 1 ml. of physiological salt solution containing 2 mg. DNP-As and 2.5 mg. Evans' blue.

The present compounds to be tested were given orally 30 minutes before antigen challenge. The animals were exsanguinated 30 minutes after challenge with the antigens and the skins were exfoliated. The intensities of PCA were evaluated by measuring the amount of leaked dye. The amount of dye leaked as a result of PCA was extracted according to the method of Harada et al [cf. Jpn. J. Allergol., Vol. 15, 1(1966)] and measured to be tested which decreased statistically significantly the amount of leaked dye comparing with control, were expressed as the minimum effect does (MED).

(2) Results

The results obtained on the PCA are shown in Table 3.

TABLE 3

| Compound | MED (mg./kg.) |
|---|---|
| Ex. 1 | 25 to 50 |
| Ex. 2 | 1.56 |
| Ex. 3 | 0.39 |
| Ex. 4 | 1.56 |
| Ex. 5 | 6.25 |
| Ex. 6 | 6.25 |
| Ex. 7 | 6.25 |
| Ex. 8 | 6.25 |
| Ex. 9 | 0.39 |
| Ex. 10 | 6.25 |
| Ex. 11 | 1.56 |
| Ex. 12 | 1.56 |

EXAMPLE 24

With respect to the 3-(1H-tetrazol-5-yl)-coumarin derivatives obtained in Examples 1 to 12, there was tested acute toxicity in mice.

After normal female Slc: ddy mice 4 weeks old were purchased and fed preliminarily in this lavoratory for a week, these mice weighing 25-27 g. were used in the test. The present compounds to be tested, were suspended in a 10% gum arabic solution and administered orally 0.1 ml./kg. body weight to mice. Each dose level was given to a group of ten animals and the survivors were kept under observation for 6 days. The numbers of dead animals were counted and the $LD_{50}$ values in mg./kg. body weight were calculated by the method of Litchfield-Wilcoxon.

The results are shown in Table 4.

TABLE 4

| Compound | $LD_{50}$ (mg./kg.) |
|---|---|
| Ex. 1 | >2000 |
| Ex. 2 | 1500-2000 |
| Ex. 3 | 1500 |
| Ex. 4 | 1500-2000 |
| Ex. 5 | 1500 |
| Ex. 6 | >2000 |
| Ex. 7 | >2000 |
| Ex. 8 | >2000 |
| Ex. 9 | >2000 |
| Ex. 10 | 1500-2000 |
| Ex. 11 | >2000 |
| Ex. 12 | >2000 |

What we claim is:

1. A tetrazolylcoumarin derivative of the following formula:

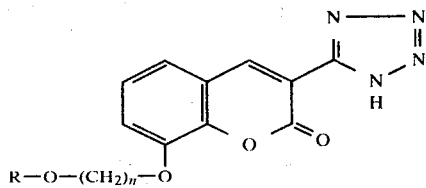

or a pharmaceutically acceptable salt thereof wherein R is a straight or branched alkyl group having 1 to 4 carbon atoms, a straight or branched alkenyl group having 2 to 4 carbon atoms, an alkoxyalkyl group of the general formula: $CH_3(CH_2)_l$—O—$(CH_2)_m$— in which l is 0 or an integer of 1 to 3 and m is an integer of 2 to 4, or phenyl group, and n is an integer of 2 to 4.

2. The tetrazolylcoumarin derivative of claim 1, which is a member selected from the group consisting of 8-(3-oxabutoxy)-3-(1H-tetrazol-5-yl)coumarin, 8-(3-oxapentyloxy)-3-(1H-tetrazol-3-yl)coumarin, 8-(3-oxahexyloxy)-3-(1H-tetrazol-5-yl)coumarin, 8-(4-methyl-3-oxapentyloxy)-3-(1H-tetrazol-5-yl)coumarin, 8-(3-oxaheptyloxy)-3-(1H-tetrazol-5-yl)coumarin, 8-(5-methyl-3-oxahexyloxy)-3-(1H-tetrazol-5-yl)coumarin, 8-(4-oxahexyloxy)-3-(1H-tetrazol-5-yl)coumarin, 8-(5-oxaheptyloxy)-3-(1H-tetrazol-5-yl)coumarin, 8-(3-oxa-5-hexenyloxy)-3-(1H-tetrazol-5-yl)coumarin, 8-(3,6-dioxaoctyloxy)-3-(1H-tetrazol-5-yl)coumarin, 8-(2-phenoxyethyloxy)-3-(1H-tetrazol-5-yl)coumarin, and their pharmaceutically acceptable salts.

3. A pharmaceutical composition having an antiallergic activity which comprises as an essential ingredient an effective amount of a tetrazolylcoumarin derivative of the following formula:

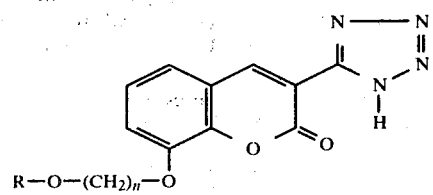

wherein R is a straight or branched alkyl group having 1 to 4 carbon atoms, a straight or branched alkenyl group having 2 to 4 carbon atoms, an alkoxyalkyl group of the general formula: $CH_3(CH_2)_l$—O—$(CH_2)_m$— in which l is 0 or an integer of 1 to 3 and m is an integer of 2 to 4, or phenyl group, and n is an integer of 2 to 4 or its pharmaceutically acceptable salt, and a pharmaceutically acceptable carrier.

4. The composition of claim 3, wherein the essential active ingredient is a member selected from the group consisting of 8-(3-oxabutoxy)-3-(1H-tetrazol-5-yl)coumarin, 8-(3-oxapentyloxy)-3-(1H-tetrazol-5-yl)coumarin, 8-(3-oxahexyloxy)-3-(1H-tetrazol-5-yl)coumarin, 8-(4-methyl-3-oxapentyloxy)-3-(1H-tetrazol-5-yl)coumarin, 8-(3-oxaheptyloxy)-3-(1H-tetrazol-5-yl)coumarin, 8-(5-methyl-3-oxahexyloxy)-3-(1H-tetrazol-5-yl)coumarin, 8-(4-oxahexyloxy)-3-(1-tetrazol-5-yl)coumarin, 8-(5-oxaheptyloxy)-3-(1H-tetrazol-5-yl)coumarin, 8-(3-oxa-5-hexenyloxy)-3-(1H-tetrazol-5-yl)coumarin, 8-(3,6-dioxaoctyloxy)-3-(1H-tetrazol-5-yl)coumarin, 8-(2-phenoxyethyloxy)-3-(1-tetrazol-5-yl)coumarin, and their pharmaceutically acceptable salts.

5. 8-(5-methyl-3-oxahexyloxy)-3-(1H-tetrazol-5-yl)coumarin.

* * * * *